United States Patent [19]

McGill et al.

[11] 4,244,365
[45] Jan. 13, 1981

[54] DEVICE FOR USE IN DETECTING OCCLUSION IN AN INFUSION SYSTEM

[75] Inventors: Lee E. McGill, Orinda; Susan J. Watkins, Berkeley, both of Calif.

[73] Assignee: Cutter Laboratories, Inc., Berkeley, Calif.

[21] Appl. No.: 23,927

[22] Filed: Mar. 26, 1979

[51] Int. Cl.³ ............................................. A61M 5/00
[52] U.S. Cl. .............................. 128/214 E; 340/626; 340/611; 73/749
[58] Field of Search ................... 128/214 E, DIG. 13; 340/616, 626, 611, 619; 73/749

[56] References Cited

U.S. PATENT DOCUMENTS

| | | | |
|---|---|---|---|
| 3,225,340 | 12/1965 | Kochey, Jr. | 340/611 |
| 3,469,574 | 9/1969 | Durkan | 128/214 E |
| 3,731,679 | 5/1973 | Wilhelmson | 128/DIG. 13 |
| 4,191,184 | 3/1980 | Carlisle | 128/214 E |

FOREIGN PATENT DOCUMENTS

| | | | |
|---|---|---|---|
| 2504792 | 8/1975 | Fed. Rep. of Germany | 128/214 |
| 2220281 | 11/1974 | France | 128/214 E |

OTHER PUBLICATIONS

Engineering Fluid Mechanics, Roberson et al., Houghton Mifflin Co., Boston, Mass. 1975, p. 21.

*Primary Examiner*—Robert W. Michell
*Assistant Examiner*—J. L. Kruter
*Attorney, Agent, or Firm*—Robert E. Allen

[57] ABSTRACT

An overpressure device is disclosed for use in a liquid infusion set for the purpose of detecting excessive pressures which may occur during infusion. The device comprises a tubular member with an inlet and an outlet, a closed pressure chamber and a bridging portion containing a small bore passage which connects the pressure chamber with the tubular member. In a preferred form, the interconnecting passage takes a tortuous path. An optical sensor positioned on the pressure chamber will detect the presence of liquid at a predetermined position in the chamber, when the liquid rises as a result of excessive pressure in the set, and respond by stopping the flow of liquid in the set.

5 Claims, 8 Drawing Figures

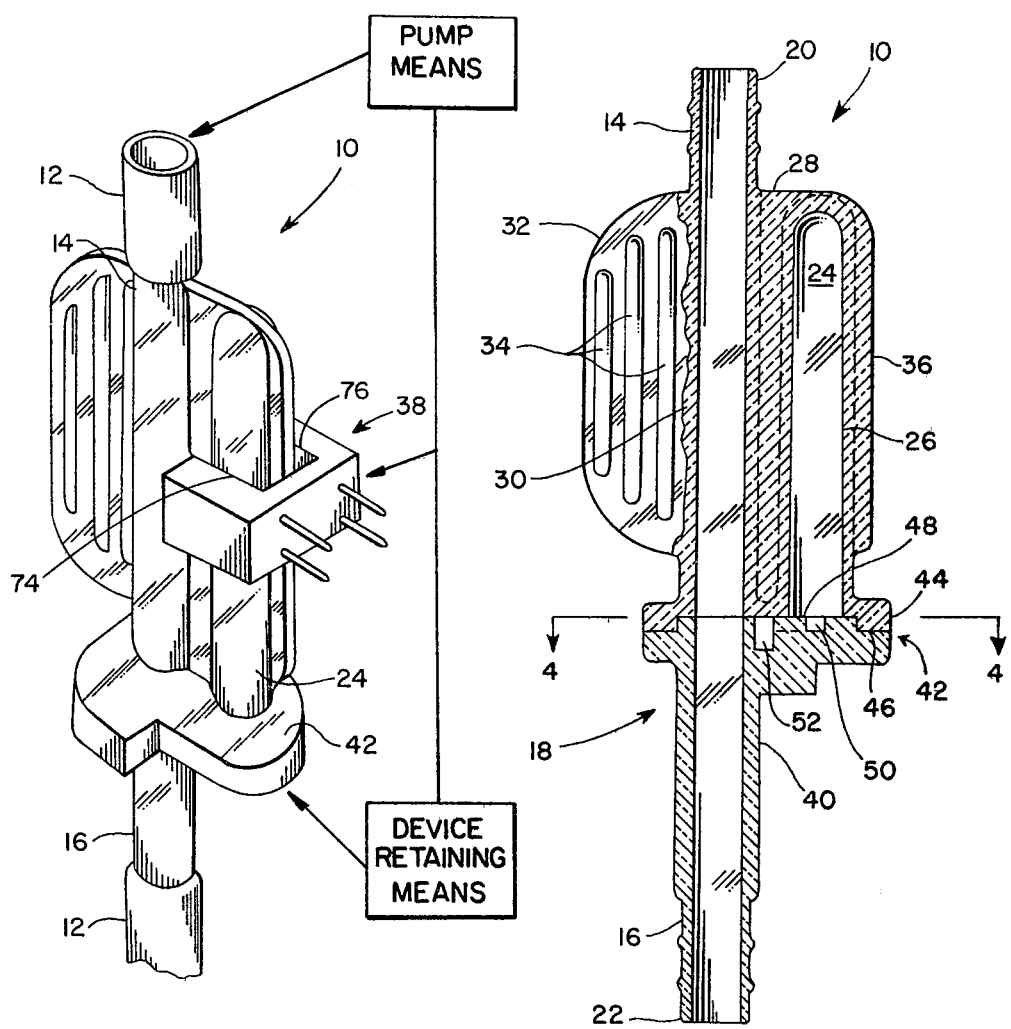

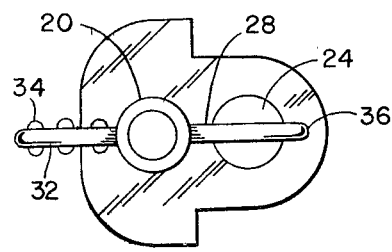
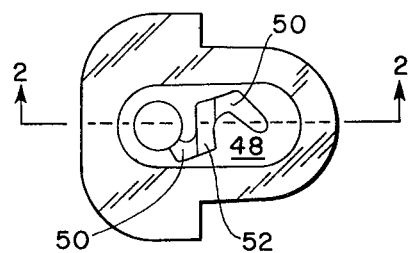
FIG. 3  FIG. 4
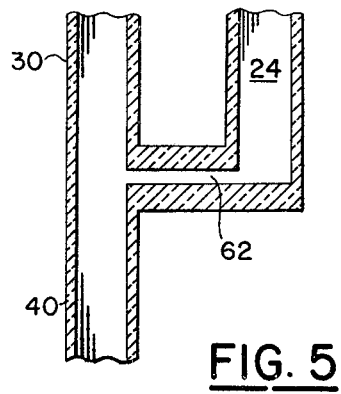
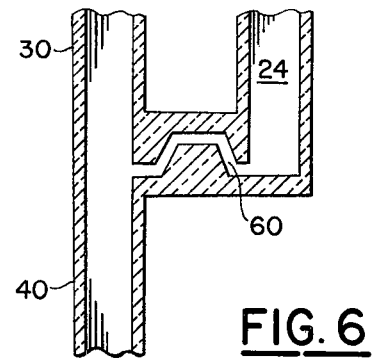
FIG. 5  FIG. 6
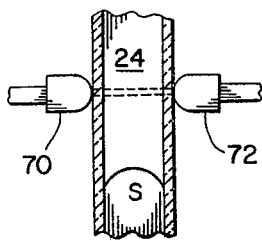
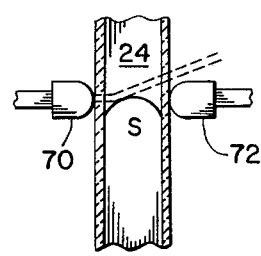
FIG. 7  FIG. 8

DEVICE FOR USE IN DETECTING OCCLUSION IN AN INFUSION SYSTEM

BACKGROUND OF THE INVENTION

1. Field

This invention relates to an overpressure device for use in a liquid infusion system to detect an overpressure condition in the system.

2. Prior Art

There are a number of intravenous solution pumps of various kinds which have been disclosed or are in use currently whose function is to deliver discrete volumes of fluids at precise rates to a patient. The use of such pumps greatly reduces the time and attention of nurses who are responsible for administration of parenteral solutions to patients as compared to the standard gravity feed system of administration where the nurse has to check constantly to see that a preadjusted flow rate is being maintained.

As sometimes happens during the administration, the tubing becomes occluded if the patient inadvertently lies on the tubing of the administration set, or the tubing may become pinched by a bed rail; or the infusion needle may become lodged into a muscle instead of the vein of the patient. If a pump were to continue forcing fluid through the tubing under such circumstances, it could result in harm to the patient.

This overpressure condition can be noted by means of auditory or visual signals built into a pump which provide a warning of the condition. There are also various means associated with I.V. pumps which sense an overpressure condition and by appropriate electrical circuitry result in stopping or greatly reducing the pumping action until the condition is corrected. One such means is disclosed in U.S. Pat. No. 3,985,133 wherein an occlusion or overpressure in a set causes a slowing down or stalling of the shaft on the pump motor. This reduction in shaft rotation is detected by a pair of light detectors which triggers the occlusion alarm. Another means for occlusion detection is disclosed in U.S. Pat. No. 3,731,679 wherein a syringe pump is associated with a device having four channels, one being connected to the pump, another to a supply of fluid, a third connected to tubing leading to the patient and the fourth being closed at its outer end. If the solution being administered becomes overpressured, it backs up into the fourth channel (which is normally filled with air) until contact is made with an electrode positioned within the channel. This activates a circuit which results in stopping the motor to the pump.

An apparatus is disclosed in U.S. Pat. No. 3,456,648 which is designed to monitor predetermined critically high levels of venous pressure during infusion of solutions. The apparatus includes a manometer connected to the tubing of the infusion set and an optical sensor slidingly supported on the manometer at any predetermined point. If the venous pressure should reach a critical pressure, the solution will rise up the manometer tube and when light from the optical sensor is reflected by the presence of the solution, a valve is actuated to stop the flow of solution into the patient. The aforementioned devices of U.S. Pat. Nos. 3,731,679 and 3,456,648 have deficiencies which prevent them from being entirely acceptable in overpressure detectors for intravenous infusion sets. They are susceptible to air being bled into the infusion line which could result in an air embolism in the patient and the sensors could be triggered if drops of solution were to come in contact with them as a result of inadvertent jarring of the devices even though no overpressure condition exists.

Formerly an I.V. pump available from Sigmamotor included th capability for detecting overpressures in an administration set. The set contained a translucent vertical connector in the tubing with a horizontal closed ended tubular branch of the same bore size extending horizontally from the middle of the connector. An optical sensor positioned intermediately on the branch detected the presence of liquid forced into this branch as a result of overpressure in the set. The major drawback with this design is again the possibility for inadvertently setting off the alarm indicating an overpressure condition should droplets be flicked into the area of the branch monitored by the sensor as a result of the unit being jarred.

These and other deficiencies are essentially eliminated by employing an improved overpressure device in an infusion set as detailed in the disclosure and claims which follow.

SUMMARY OF THE INVENTION

The overpressure device of the present invention comprises a tubular member with an inlet and an outlet adapted for connection with tubing of an infusion set. A generally upstanding hollow column or pressure chamber closed at its upper end is connected at its lower end to an intermediate position on the tubular member by a transverse bridging portion containing an interconnecting passage whose bore is substantially smaller than the bore of either the pressure chamber or the tubular member. The bore of the passage in the bridging portion is preferably tortuous and a most preferred form is one in which the bridging portion contains a cavity communicating with the passage.

When the infusion set is connected to a supply of intravenous solution and attached to an infusion pump and the set cleared of air by priming with the solution, the over-pressure device portion of the set is then normally secured to the pump unit so that the pressure chamber portion of the device is positioned in an optical sensor associated with the pump. The solution fills the tubular member portion of the device and, because there is normally a small head pressure resulting from the extension of the set above the level of the pump, the pressure will force a small amount of the solution into the passage of the bridging portion but not into the pressure chamber which is full of air. When the pump is in operation, should a condition arise when pressure in the infusion set rises to a point which could be detrimental to the patient, as for example, a pressure of 10 to 15 p.s.i. above atmospheric pressure, the solution will compress the air and rise up into the pressure chamber. When the meniscus of the solution reaches the point where the light beam from the optical sensor is deflected away from the photodetector of the sensor, the circuitry of the sensor is altered and responds by shutting off the pump and turning on a visual or audio alarm.

The bore of the passage in the bridging portion is of a size such that the surface tension of the solution being infused will inhibit flow into the pressure chamber portion under normal pressures. During priming operations, the device normally is tapped to help clear it of air along its flow path. This small bore passage inhibits a liquid from accumulating at the bottom of the pressure chamber, which if it were present could cause droplets of the liquid being splashed upwardly into the path of the optical sensor to trigger the overpressure alarm. Inadvertent jarring of the pump while it is in operation could produce the same effect and shut down the pump if there were a small amount of liquid at the bottom of the pressure chamber. A tortuous path for the passage is superior to one which is straight since it would be essentially impossible for a liquid to be splased inadvertently into the pressure chamber. Preferably, a small reservoir or cavity communicates with the passage and allows bore size to remain small while taking up the small amount of liquid forced into the passage by the slight head pressure of the liquid in the infusion set, thus keeping the pressure chamber free of the liquid.

The invention can be better understood and the advantages will become apparent from the following description of some preferred embodiments and as illustrated by the drawings.

BRIEF DESCRIPTON OF THE DRAWINGS

FIG. 1 is a view in perspective of an overpressure device and with an optical sensor positioned on the device.

FIG. 2 is side view in partial cross section of an embodiment of the overpressure device of this invention, the lower portion shown in section taken along the line 2—2 of FIG. 4.

FIG. 3 is a top view of the device of FIG. 2.

FIG. 4 is a view taken along the line 4—4 of FIG. 2.

FIG. 5 is cross sectional view of a portion of another embodiment of the overpressure device.

FIG. 6 is a cross sectional view of a portion of still another embodiment of the overpressure device.

FIG. 7 is a side view of an intermediate portion of the pressure chamber in the overpressure device illustrating an uninterrupted beam of light passing through the chamber.

FIG. 8 is a view similar to that of FIG. 7 but with the beam of light reflecting off the surface of liquid in the chamber.

DETAILED DESCRIPTION OF PREFERRED EMBODIMENTS

Referring to the drawings, FIG. 1 shows an overpressure device 10 as part of an infusion set which is connected by tubing 12 at its upper end 14 to a source of supply of an infusion solution (not shown) and at its lower end 16 to an infusion needle or catheter (not shown). As more clearly seen in FIG. 2 device 10 has an elongated tubular portion 18 with inlet 20 and outlet 22 adapted for connection to tubing 12.

A pressure chamber 24 formed by walls 26 and closed at the top is supported by a ridge 28 connecting to an upper portion 30 of the tubular member 18. The pressure chamber walls should be made of either transparent or translucent material so that light can pass through the chamber. The device 10 may have a handle 32 with ribs 34 for convenience in grasping the device when locking it into an I.V. pump. A positioning rib 36 extending along chamber 24 may be included to assist in aligning an optical sensor 38 at an appropriate point as will be described in greater detail subsequently.

Lower portion 40 of tubular member 18 is joined to the upper portion 30 by a bridging portion 42 formed by sealing shoulder 44 of the upper portion to a ledge 46 on the lower portion. The upper surface 48 of the lower portion 40 has a channel 50 of a size substantially smaller in cross section than the bores in the tubular member 18 and the pressure chamber 24. Channel 50 connects chamber 24 with the interior of tubular member 18 by a tortuous passage shown in FIG. 4 as a preferred form of this embodiment for the overpressure device. An alternate form of a tortuous passage 60 is illustrated in FIG. 6. This narrow bore passage can also be straight like passage 62 as in FIG. 5 but tortuous passages are generally preferred for the reason stated above. As shown in FIGS. 2 and 4, channel 50 preferably includes a small reservoir or cavity 52 intermediate between the ends of channel 50 which in this instance is provided by a deeper cut into channel 50.

An optical sensor 38 normally is secured at an appropriate position on an I.V. pump so that the overpressure device 10 can be positioned with the pressure chamber 24 aligned with the optical sensor at a fixed location so that the sensor will react to an overpressure condition of a predetermined magnitude. The shelving of the intermediate bridging portion 42 can function as engagement means to secure the device to the I.V. pump as by corresponding slots or clamps associated with the pump. The optical sensor 38 has a light emitting diode 70 and a photodector 72 opposite each other in the side walls 74 and 76. A typical optical sensor is that available from HEI Products, Chafka, Minnesota. The light beam from the emitter 70 normally passes through the walls of chamber 24 in a straight path to be received by the detector 72 since chamber 24 contains only air during the normal operation of the pump. In the event pressure in the infusion set increases to a magnitude which forces solution S into chamber 24 until the liquid level reaches the point shown in FIG. 8, the light beam is deflected away from the detector 72. The circuitry of the optical sensor is designed to interact with the circuitry of the pump motor and shut it off in this situation as well as actuate an audio or visual alarm. Such circuitry and alarm features are well known in the art and therefore are not detailed here.

Several examples of the overpressure device of the present invention having been disclosed; these should be construed as illustrative only and the scope of the invention is intended to be limited only by the following claims.

We claim:

1. In an infusion set for administering parenteral solutions, the set having flexible tubing with means for connecting to a supply of parenteral solution at one end and to an infusion needle at the other end, an intermediate portion of the tubing to which pumping means can be associated for driving the solution through the set, the set having an overpressure device connected to the tubing at a point between the pumping means and the infusion needle, the improvement in the overpressure device which comprises a tubular member with an upper portion and a lower portion having an inlet at its upper portion and an outlet at its lower portion with the inlet and the outlet being connected with the tubing at the point between the pumping means and the infusion needle, the over-pressure device including a pressure chamber generally vertically inclined, closed at its upper end and joined at its lower end to an intermediate position on the tubular member by a transverse bridging portion which contains an interconnecting passage whose bore is substantially smaller than bores of either the pressure chamber or the tubular member, whereby in an overpressure condition a portion of the solution will be forced through the interconnecting passage and rise into the pressure chamber to a point where transmitted light from an optical sensor positioned at the pressure chamber is deflected by the meniscus of the solution, interrupting the light being sensed by a receiver of the optical sensor and communicating the interruption to the pumping means to cause inactivation of the pumping means.

2. The device of claim 1 wherein the bore of the interconnecting passage takes a tortuous path.

3. The device of claim 3 wherein the bridging portion further contains a small reservoir which communicates with the interconnecting passage.

4. The device of claim 1 further including engagement means for positioning the device to device retaining means associated with the pumping means.

5. In an infusion set for administering parenteral solutions, the set having flexible tubing with means for connecting to a supply of parenteral solution at one end and to an infusion needle at the other end, an intermediate portion of the tubing to which pumping means can be associated for driving the solution through the set, the set having an overpressure device connected to the tubing at a point between the pumping means and the infusion needle, the improvement in the overpressure device which comprises a tubular member with an upper portion and a lower portion having an inlet at its upper portion and an outlet at its lower portion with the inlet and the outlet being connected with the tubing at the point between the pumping means and the infusion needle, the overpressure device including a pressure chamber generally vertically inclined, closed at its upper end and joined at its lower end to an intermediate position on the tubular member by a transverse bridging portion which contains an interconnecting passage whose bore is substantially smaller than bores of either the pressure chamber or the tubular member, the interconnecting passage taking a tortuous path and with the bridging portion further containing a small reservoir which communicates with the interconnecting passage, whereby in an overpressure condition a portion of the solution will be forced through the interconnecting passage and rise into the pressure chamber to a point where transmitted light from an optical sensor positioned at the pressure chamber is deflected by the meniscus of the solution, interrupting the light being sensed by a receiver of the optical sensor and communicating the interruption to the pumping means to cause inactivation of the pumping means.

* * * * *

UNITED STATES PATENT AND TRADEMARK OFFICE
CERTIFICATE OF CORRECTION

PATENT NO. : 4,244,365
DATED : January 13, 1981
INVENTOR(S) : LEE E. MCGILL ET AL It is certified that error appears in the above-identified patent and that said Letters Patent are hereby corrected as shown below:

Column 3, line 9, change "splased" to --splashed--.

Column 5, line 10, change numeral "3" after "claim" to --2--.

Signed and Sealed this

Twenty-first Day of April 1981

[SEAL]

Attest:

RENE D. TEGTMEYER

*Attesting Officer*  *Acting Commissioner of Patents and Trademarks*